United States Patent [19]
Giddings

[11] Patent Number: 5,156,039
[45] Date of Patent: Oct. 20, 1992

[54] PROCEDURE FOR DETERMINING THE SIZE AND SIZE DISTRIBUTION OF PARTICLES USING SEDIMENTATION FIELD-FLOW FRACTIONATION

[75] Inventor: John C. Giddings, Salt Lake City, Utah

[73] Assignee: University of Utah, Salt Lake City, Utah

[21] Appl. No.: 640,959

[22] Filed: Jan. 14, 1991

[51] Int. Cl.[5] ............................................. G01C 25/00
[52] U.S. Cl. ....................................................... 73/1 R
[58] Field of Search ...................... 73/1 R, 61.4, 865.5; 436/70

[56] References Cited

U.S. PATENT DOCUMENTS

| | | | |
|---|---|---|---|
| 2,693,706 | 11/1954 | Carpenter et al. | 73/865.5 |
| 4,193,288 | 3/1980 | Berber et al. | 73/1 R |
| 4,283,276 | 8/1981 | Grant | 73/865.5 |
| 4,285,809 | 8/1981 | Dilks, Jr. et al. | 73/865.5 |
| 4,331,862 | 5/1982 | Ryan | 73/1 R |
| 4,434,647 | 3/1984 | Whitcomb et al. | 73/1 R |

Primary Examiner—Hezron E. Williams
Assistant Examiner—George M. Dombroske
Attorney, Agent, or Firm—Terry M. Crellin

[57] ABSTRACT

A procedure for determining particle size and particle size distribution data from sedimentation field-flow fractionation comprises carrying out a calibration run in which a sample of particles of known density and size is injected into a liquid carrier stream flowing through a field-flow fractionation channel. The acceleration G acting on the calibration sample during the calibration run and the density difference $\Delta\rho$ between the particles of the calibration sample and the liquid carrier of the calibration run are known. Retention time or retention volume of the particles of different known sizes are measured during the calibration run. The retention times or retention volumes are used to develop a calibration relationship expressing retention time or retention volume as a function of particle size. In a test run, a test sample of particles is injected into the liquid carrier stream flowing through the channel. The density difference $\Delta\rho'$ between the test particles and the liquid carrier stream is known, but the test particles have sizes and a size distribution that are unknown. The acceleration G' acting on the test sample is adjusted so that the product $G'\Delta\rho'$ for the test run is the same as the product $G\Delta\rho$ for the calibration run. The relative concentration of test particles eluted at different times in the test run is determined, and this relative concentration determination is combined with the calibration relationship to calculate the particle sizes and the particle size distribution of the particles in the test sample.

17 Claims, 6 Drawing Sheets

PROCEDURE FOR DETERMINING THE SIZE AND SIZE DISTRIBUTION OF PARTICLES USING SEDIMENTATION FIELD-FLOW FRACTIONATION

BACKGROUND OF THE INVENTION

1. Government Support

This invention was made with Government support under Public Health Service Grant GM10851-33 awarded by the National Institutes of Health. The Government has certain rights in the invention.

2. Field of the Invention

The present invention relates to a procedure for determining the particle size and size distribution of a sample of particles, referred to herein as test particles, using a sedimentation field-flow fractionation process. In particular the present invention relates to the use of a novel calibration system in combination with a field-flow fractionation process for determining the size and size distribution of particles in a test sample.

3. State of the Art

Field-Flow fractionation (FFF) consists of a great number of operating modes and subtechniques, each having its own unique characteristics and range of applicability. For example, the normal mode of FFF, whether the applied field is sedimentation, thermal, crossflow, or electrical, is applicable to macromolecules and particles up to about 1 $\mu$m in diameter, or in special circumstances up to 3 or 4 $\mu$m in diameter. The dependence of retention on particle size or mass in the normal mode is generally quite predictable, providing the force exerted on the sample particles by the applied field is a calculable quantity. In the normal mode of sedimentation FFF, for example, the retention time can be calculated with reasonable accuracy from well known transport equations for particles of known size and density. Thus, particle size distributions can be obtained from experimental fractograms (detector response vs. time curve) on the basis of theoretical relationships without recourse to the use of calibration standards.

The steric mode of operation of FFF, in contrast to normal FFF, does not yield unknown particle diameters unless subject to empirical calibration, even if the applied force acting on the particles can be calculated. The reason calibration is needed is that the relatively large (over 1 $\mu$m in diameter) particles subject to steric FFF are substantially influenced by hydrodynamic effects, particularly by hydrodynamic lift forces that tend to drive the particles away from the wall at which they normally accumulate. By altering the particle-wall distance in the FFF channel, these forces disturb the particle migration rate. While hydrodynamic lift forces have been studied at great length by many investigators, there are at the present time no simple theoretical expressions that predict the magnitude of these forces as a function of particle diameter, shear rate, and the distance of the particle from the accumulation wall. Thus, particle retention cannot be directly calculated when lift forces are substantial.

Calibration is thus a necessity in steric FFF. Calibration offers the only really effective method of routinely determining particle size and particle size distribution of samples subjected to FFF. Unfortunately, however, a suitable calibration procedure that is applicable to particles of different densities has not heretofore been disclosed in the art.

4. Objectives

A principal objective of the invention is to provide a novel procedure for determining particle size and size distribution of particles in samples subjected to sedimentation FFF process.

A further objective of the present invention is to provide a simple but very accurate method for determining the particle size and size distribution of test particles using sedimentation/steric FFF.

It is a still further objective of the present invention to provide a new calibration technique for use with an FFF channel for determination of particle size and size distribution for particles eluted from the FFF channel, with the calibration technique being based on a density compensation procedure.

BRIEF DESCRIPTION OF THE INVENTION

The above objectives are achieved in accordance with the present invention by providing a new procedure for determining particle size and size distribution of test samples using FFF procedures combined with a novel, new calibration technique that is based on a density compensation procedure. The new procedure for determining the size and size distribution of test particles comprises injecting a sample of test particles into a liquid carrier stream flowing through a test sedimentation field-flow fractionation channel. A novel calibration method is used to calibrate the test channel so that particle size and size distribution can be quickly and accurately determined without requiring microscopic analysis of the eluted fractions from the FFF channel.

It has been found that by utilizing a balance between driving and lift forces as a calibration sample of known particle size and the test sample of unknown particle size flow through the FFF channel, equal retention in the channels will result for equal size particles subject to equal driving forces irrespective of particle density. Therefore, by adjusting the rotation rate of the FFF channel to exactly compensate for density, retention can be brought in line with that of standards, a conclusion verified by microscopy. Calibration relationships such as linear plots of the log of retention time or the log of retention volume versus the log of particle diameter can be produced that permit rapid, accurate calculation of the particle size and size distribution of samples of test particles.

The calibration is achieved by carrying out at least one calibration run in an FFF channel through which a liquid carrier stream flows. At least one calibration sample of calibration particles of known density and size distribution is injected into the liquid carrier stream flowing through the calibration FFF channel. The acceleration G acting on the calibration sample during the calibration run and the density difference $\Delta\rho$ between the calibration particles of the calibration sample and the liquid carrier of the calibration run are known so that the product $G\Delta\rho$ for the calibration run has a determined value. The calibration channel can be the test channel that is to be used in test runs with samples of the test particles or it can be a duplicate channel having essentially the same dimensions as the test channel. In addition, the calibration channel can be one that is similar to the test channel, i.e., having a thickness that is about the same as the thickness of the test channel, if the linear velocity of the liquid carrier in the similar calibration channel is maintained essentially the same as the linear velocity of the liquid carrier in the test channel.

Retention time or retention volume of calibration particles of different known sizes in the calibration sample is measured. Retention time is defined as the time that passes between injection of the sample of particles into the liquid carrier flowing through the channel and the detection of particles of the particular size being eluted from the channel. Retention volume is defined as the volume of liquid carrier flowing out of the channel during the time period between injection of the sample of particles and the elution of particles of particular sizes from the channel. The measured retention times or retention volumes are then used to develop a calibration relationship expressing retention time or retention volume as a function of particle size.

This calibration relationship can then be used to determine the size and size distribution of test particles injected into the test FFF channel during test runs. In a test run, a test sample of test particles is injected into the liquid carrier stream flowing through the test channel. The density difference $\Delta\rho'$ between the test particles and the liquid carrier stream flowing in the test channel is known, but the test particles have sizes and a size distribution that are unknown.

The acceleration $G'$ acting on the test sample during the test run is adjusted such that the product $G'\Delta\rho'$ for the test run is the same as the product $G\Delta\rho$ for the calibration run. The relative concentration of test particles eluted at different times in the test run is determined, and the relative concentration is combined with the calibration relationship to calculate the particle sizes and the particle size distribution of the particles in said test sample.

Additional objects and features of the invention will become apparent from the following detailed description, taken together with the accompanying drawings.

THE DRAWINGS

Various embodiments of the present invention representing the best mode presently contemplated of carrying out the invention are illustrated in the accompanying drawings in which.

DETAILED DESCRIPTION OF PREFERRED EMBODIMENTS

For better understanding of the invention, a general discussion of the theory involved will be given prior to presenting particular embodiments and experimental results.

The particle size distribution $m(d)$, expressing the mass m of particulate matter lying in a unit range of particle diameter d, is given by equation (1). This equation is disclosed and fully described in Giddings et al *Colloid and Interface Science*, Vol. 1V, 1976, pages 318-398.

$$m(d) = c(t_r)|dV_r/dd| \tag{1}$$

In equation (1), $c(t_r)$ is the fractogram function representing the mass concentration c of particulate matter emerging at retention time $t_r$ per unit volume of channel effluent and $V_r$ is the retention volume. Equation (1) can be transformed to $$m(d) = c(t_r)(dV_r/dt_r|dt_r/dd| = c(t_r)\dot{V}|dt_r/dd| \tag{2}$$

where $\dot{V}$ represents the flowrate through the channel. The absolute value bars are used because retention time $t_r$ or $V_r$ may either increase (normal mode of FFF) or decrease (steric FFF) with d without effecting the validity of the above equations.

Equations (1) and (2) show that the particle size distribution function $m(d)$ can only be obtained from the fractogram function $c(t_r)$ if the retention time $t_r$, or equivalently, the retention volume $V_r$, is a known function of particle diameter d so that $dt_r/dd$ may be obtained. In normal FFF, this dependency is obtained from theory; in steric FFF, the relationship between $t_r$ and d must be obtained by empirical calibration. The precise form of this function is unimportant mathematically, and the way it is obtained is of no significance as long as a valid relationship is know so that $dt_r/dd$ can be obtained.

For steric FFF a plot of log $t_r$ versus log d normally yields a straight line. This straight line relationship can be expressed by $$\log t_r = -S(\log d) + \log t_{r1} \tag{3}$$

or if $t_r$ is tabulated as the dimensionless ratio $t_r/t^0$, by $$\log(t_r/t^0) = -S(\log d) + \log t_{r1}/t^0) \tag{4}$$

where S, the negative slope of the plot, is equal to the particle diameter selectivity, $|d \log (t_r)/d \log (d)|$, $t^0$ is the void time and $t_{r1}$ is a constant equal to the extrapolated value of $t_r$ for particles of unit diameter. These equations can be expressed in the alternate form $$t_r = t_{r1}/d^S \tag{5}$$

As long as equations (3), (4) and (5) are valid, the derivative term in equation (2) becomes $$dt_r/dd = -St_{r1}d^{-(S+1)} \tag{6}$$

When equation (6) is substituted into equation (2), the following equation (7) is obtained $$m(d) = c(t_r)\dot{V}St_{r1}/d^{S+1} = c(t_r)\dot{V}St_{r1}(t_r/t_{r1})^{(S+1)/S} \tag{7}$$

where the minus sign has disappeared because of the absolute value designation in equation (2). The latter expression of equation (7) can be used directly to obtain $m(d)$ from the fractogram function provided the constant S and $t_{r1}$ are known.

In utilizing the theoretical principles discussed above, the first step of the new procedure of the present invention is to develop a calibration relationship for the FFF channel. This is done by carrying out at least one calibration run in which one or more samples of calibration particles of known density and size is injected into a liquid carrier stream flowing through a calibration FFF channel. The calibration relationship is one which expresses a function between diameter d of the calibration particles and retention time $t_r$ or retention volume $V_r$ of the calibration particles in the channel during the calibration run. This function must be one that applies to a specific value of the product $G\Delta\rho$, wherein G is the acceleration and $\Delta\rho$ is the density difference between the calibration particles and the liquid carrier stream into which the calibration particles are injected during the calibration run. Preferred functions comprise calibration curves in which log $t_r$ or log $V_r$ is plotted against log d. Alternatively, however, the calibration functions may be of any other graphic, analytical or numerical relationship between $t_r$ and the diameter d of the calibration particles or between $V_r$ and the diameter d of the calibration particles, wherein the relationship is developed from experimental calibration runs of the calibration particles through the FFF channel.

The second step is to carry out at least one test run in which a sample of the test particles of unknown size and size distribution is injected into a liquid carrier stream flowing through the test FFF channel. The test channel can be the calibration channel or a duplicate channel having essentially the same dimensions as the calibration channel. Alternatively, the test channel can be a channel similar to the calibration channel. A similar channel is one that has a thickness which is essentially the same as the thickness of the calibration channel. When a similar channel is employed, the linear velocity of the liquid carrier in the similar channel must be maintained essentially the same as the linear velocity of the liquid carrier in the calibration channel during the calibration run or runs.

The acceleration G' acting on the test sample of particles during each test run is adjusted such that the product $G'\Delta\rho'$ for the test run is the same as the product $G\Delta\rho$ for the calibration run or runs. Consistent with the calibration run or runs, $\Delta\rho'$ is the density difference between the test particles and the liquid carrier stream into which the test particles are injected during the test run or runs. Any suitable carrier liquid can be used as long as the liquid is inert chemically with respect to the particles. Preferably, carrier liquids include distilled water containing suitable detergents for particle stabilization and chemicals, such a sodium azide, as a bactericide.

The third step of the procedure of the present invention includes passing the eluted test particle fractions through a detector that provides a record of relative particle concentration of test particles as a function of retention time or retention volume. A representative detector is disclosed in the Example of the procedure that follows hereafter.

The last step of the procedure of the present invention is to combine the relative concentration determination, i.e., the detector response, with the calibration relationship to calculate the particle sizes and the particle size distribution of the particles in the test sample. Specifically, a fractogram can be prepared comprising a graph of the detector response plotted against retention time or retention volume, giving the relative concentration of the fractions eluted from the FFF channel. The particle diameter from the calibration relationship can be superposed on the retention time or retention volume scale of the fractogram to yield particle diameter and allow the calculation of particle size distribution.

It is not necessary to actually plot the fractogram and the graph of retention time or retention volume as a function of particle diameter. Instead, the detector responses representing the relative concentration of the fractions and the data relating the retention time or retention volume as a function of diameter is used with the equations given above, in particular equations 3, 4 and 7, to calculate the particle sizes and the particle size distribution of the test sample.

The following example is given to illustrate the operation of the claimed calibration procedure as well as to demonstrate the accuracy of the new procedure. It should be understood, however, that the example is given only for illustration and is not to be regarded as limiting the invention as claimed in the following claims in any way.

EXAMPLE

The equipment used in this example was a sedimentation FFF rotor unit similar to the unit disclosed in T. Koch and J. C. Giddings, *Anal. Chem.* 58 994 (1986) and has the same basic structure as model S101 colloid/particle fractionator from FFF Fractionation, Inc. of Salt Lake City, Utah. These systems all have a horizontal spin axis (a vertical spin plane) to prevent larger particles from settling to the edges of the channel during the run due to gravitational sedimentation.

Two different channels were used in different runs of this example to verify the generality of the new calibration procedure. Channel I was a conventional FFF channel which was uniform in cross section from end to end. Channel I had a tip-to-tip length of 92 cm, a breadth of 2 cm and a uniform thickness of 254 $\mu$m. The void volume, measured as the elution volume of a non-retained sodium benzoate peak, was 5.1 mL.

Channel II was a specialized FFF channel incorporating a novel pinched inlet design as disclosed in J. C. Giddings, *Sep. Sc. Technol.* 24 755 (1989), in which the first 40% of the channel length is a uniform 127 $\mu$m thick as compared to the 254 $\mu$m thickness of the remainder of the channel. Channel II had a total length of 90 cm and a breadth of 2 cm similar to channel I.

The standards (particles) used for calibration were polystyrene latex beads (Duke Scientific, Palo Alto, Cal.) with reported diameters of 47.9, 29.12, 19.58, 15.0, 9,87, 7.04 5.002, 3.983 and 2.062 $\mu$m (hereinafter described as 48, 29, 20, 15, 10, 7, 5, 4 and 2 $\mu$m, respectively). Two polydisperse glass bead samples were used to demonstrate the new calibration procedure for size characterization. A nominal 5-50 $\mu$m material from Duke Scientific and a 5-30 $\mu$m sample from NIST(SRM 1003) were used. The glass bead samples were treated with a density flotation method to rid them of beads containing bubbles. This density fractionation was achieved using 1,4-diiodobutane with a density of 2.35 g/mL. The resulting high density glass bead samples were cleaned with ethyl alcohol and the aqueous carrier several times. Samples having volumes of 70–80 $\mu$L of well-stirred 35 mg/mL glass bead suspensions were injected for each run.

For channel I, the sample was injected directly into the channel inlet using a microsyringe. The carrier flow was then interrupted (following the stopflow procedure) and the centrifuge set spinning to achieve the sample relaxation. Flow was then resumed. For channel II, whose structure is designed to make the stopflow procedure unnecessary, the channel was first brought up to its final rotational speed and the sample was introduced into the continuously flowing stream entering through the inlet tubing and seal.

The carrier liquid used for these experiments was doubly distilled water with 0.01% FL-70 detergent used for particle stabilization and 0.02% sodium azide used as a bactericide. The carrier flow was driven by an FMI Lab Pump, model QD-2.

The eluted sample was monitored at 254 nm by an Altex model 153 UV detector. A strip chart recorder was used for recording the detector output. Particle fractions were collected using a model FC-80K microfractionator from Gilson Medical Electronics. These samples were then examined by microscopy.

Figure 1:
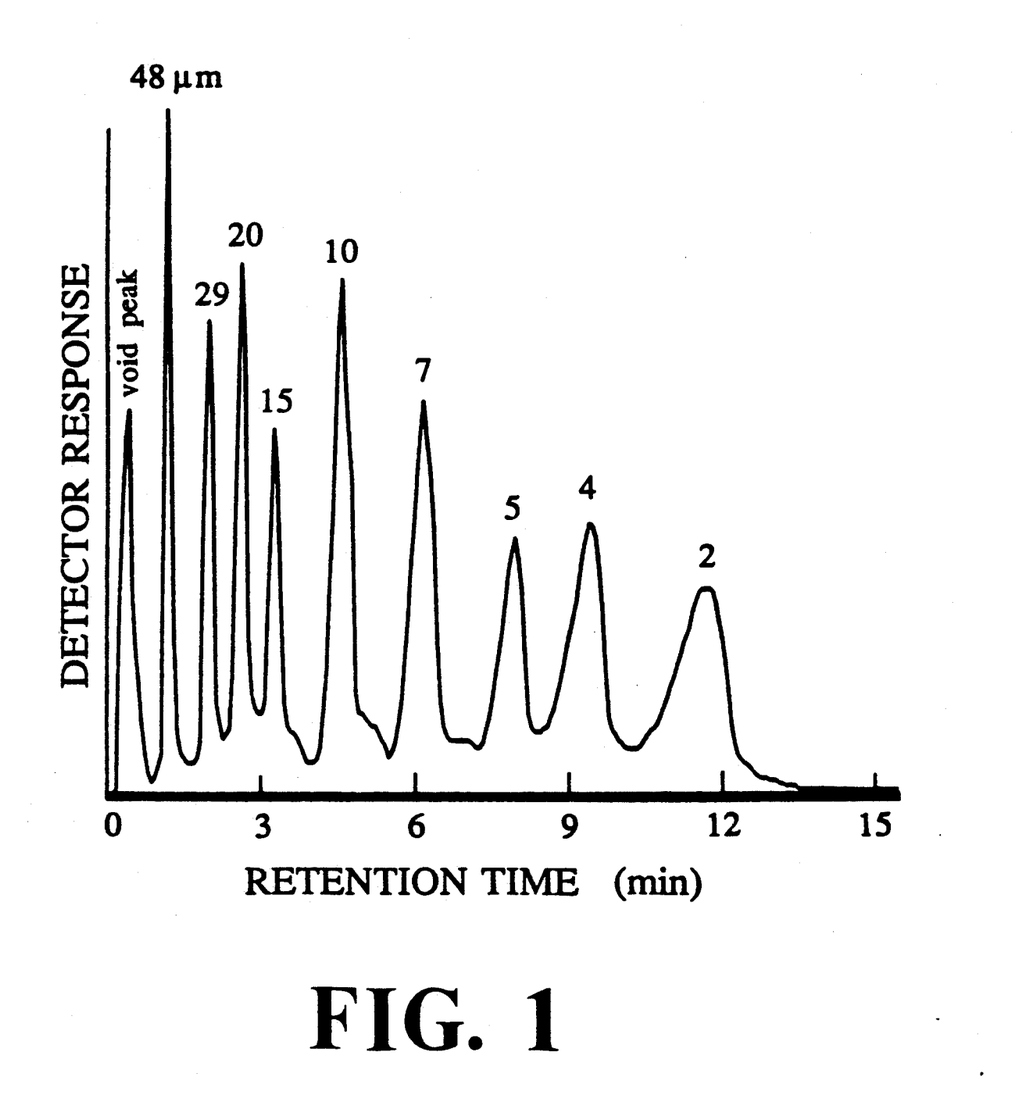
FIG. 1 is a fractogram showing the separation of nine polystyrene latex standards of the indicated diameters in a FFF channel at 800 rpm and a flow rate of 10.3 mL/min.

Calibration curves were established by measuring the retention times of each of a series of latex beads under specified conditions. Retention times can be accurately measured because latex microspheres of different diameter form sharp peaks as illustrated in the fractogram of FIG. 1. This fractogram was obtained by running a sample consisting of a mixture of nine latex standards (particles) of different diameters through channel II and illustrates the high resolution that can be achieved in particle size analysis using sedimentation/steric FFF.

Figure 2:
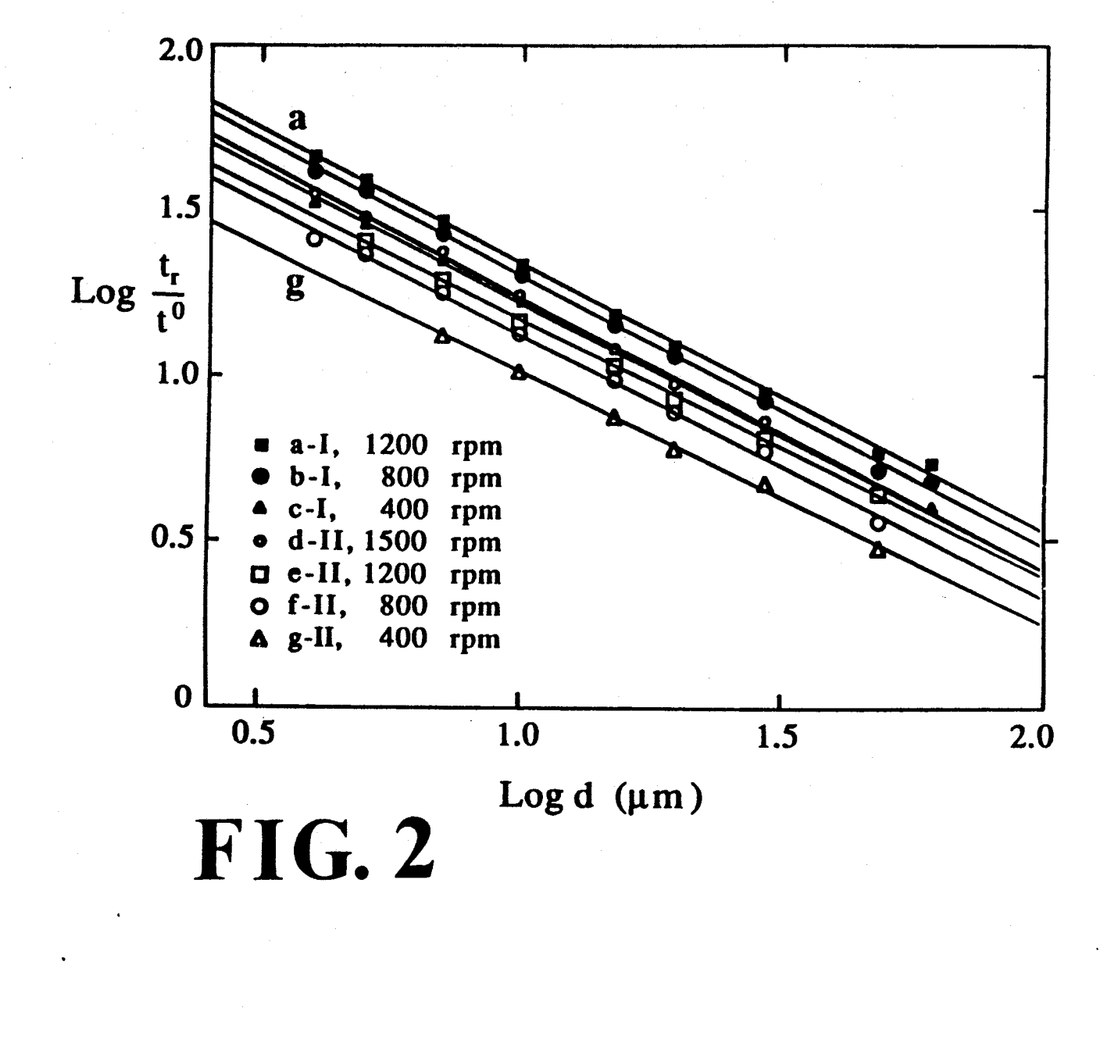
FIG. 2 is a graph showing the least square linear calibration curves for polystyrene latex standards obtained at a flow rate of 10.3 mL/min.

A series of seven calibration plots are shown in FIG. 2. The plots correspond to different rotation rates applied to the two different channel systems as specified in Table I. All runs were made at a flowrate of 10.3 mL/min. The straight lines shown in the figure were obtained by least squares. The slope ($-S$) and the intercept ($t_{r1}/t^0$) are also shown in Table I.

TABLE I

Experimental Conditions and Parameters Corresponding to Calibration Plots of FIG. 2*

| plot | channel | rpm | $G \times 10^{-4}$ (g/cm$^2$s$^2$) | S | $t_{r1}/t^0$ |
|------|---------|------|--------|-------|-------|
| a | I | 1200 | 1.244 | 0.813 | 140.6 |
| b | I | 800 | 0.553 | 0.823 | 132.4 |
| c | I | 400 | 0.138 | 0.812 | 106.4 |
| d | II | 1500 | 1.943 | 0.824 | 113.5 |
| e | II | 1200 | 1.244 | 0.780 | 88.3 |
| f | II | 800 | 0.553 | 0.796 | 82.2 |
| g | II | 400 | 0.138 | 0.764 | 58.9 |

*all flowrates = 10.3 mL/min

The plots displayed in FIG. 2 (and tabulated in Table I) consist only of the linear portions of the logarithmic time-diameter relationship corresponding to fully developed steric FFF. As one proceeds left along any given plot (in the direction of smaller particle diameter), the steric transition region is encountered. As one proceeds into this region, Brownian motion, as characteristic of the normal operating mode of FFF, plays an increasing role in driving particles away from the accumulation wall. This effect leads to earlier elution than would be expected on the basis of steric effects alone. Therefore, the plots begin to bend downward (toward shorter retention times) upon proceeding through a maximum at the steric transition point. The retention of particles of still smaller diameter is governed largely by normal FFF, but a significant steric influence persists well beyond the transition point.

Figure 3:
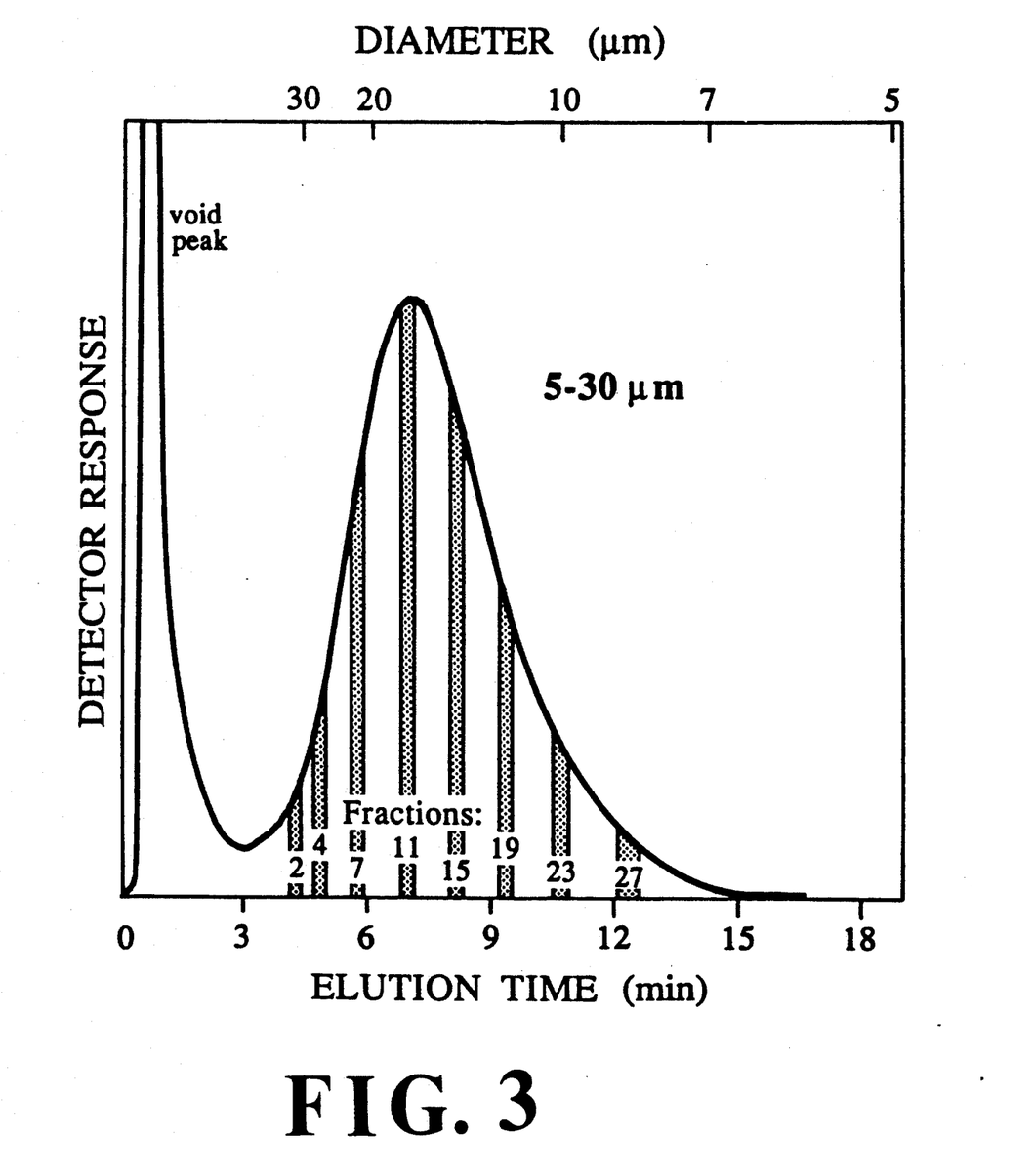
FIG. 3 is a fractogram of polydisperse 5-30 μm glass bead sample in an FFF channel at 224 rpm, a flow rate of 10.3 mL/min. and a stopflow time of 2 seconds.
Figure 4:
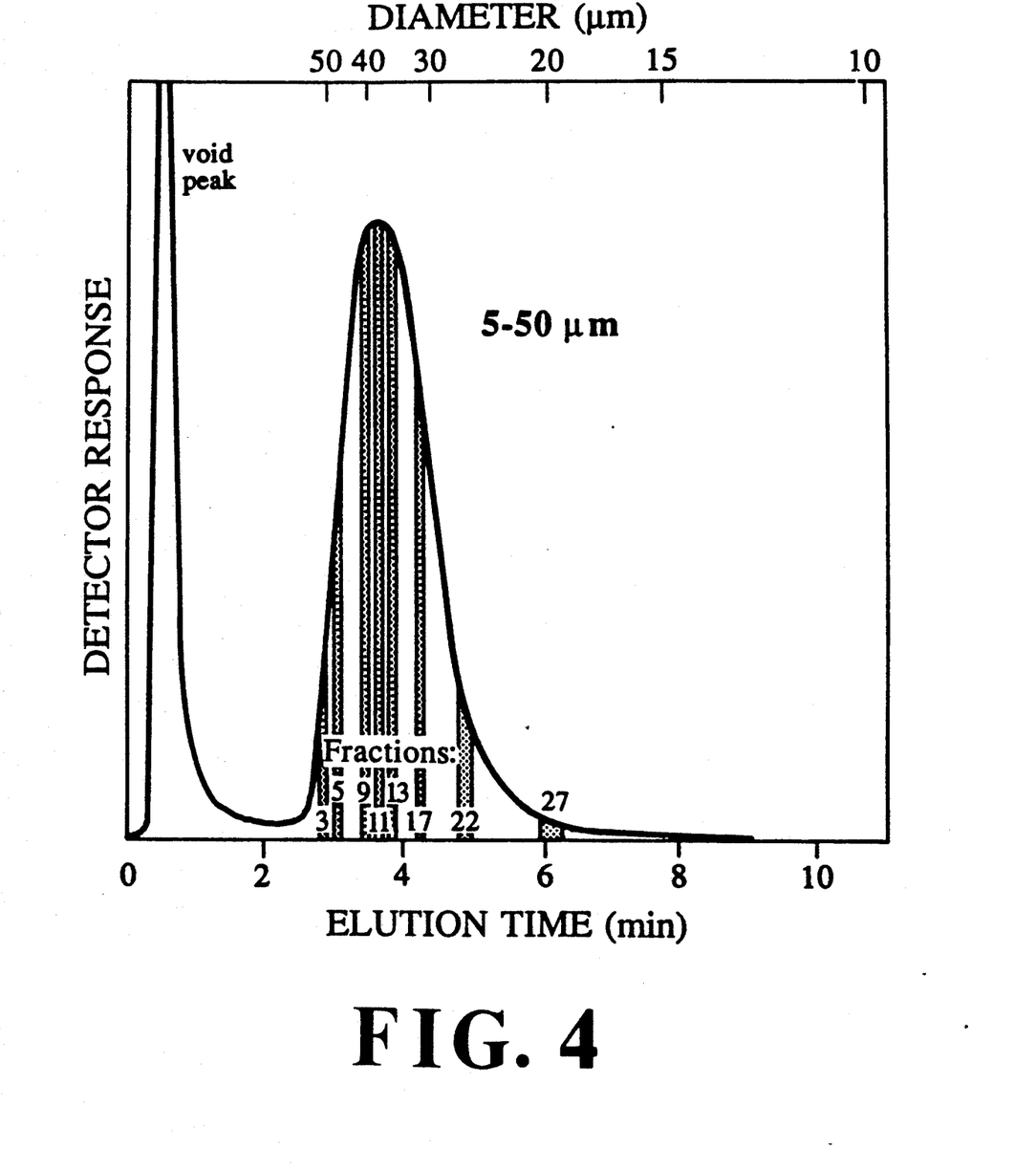
FIG. 4 is a fractogram of a 5-50 μm glass bead sample in an FFF channel at 222 rpm, a flow rate of 10.3 mL/min. and a stopflow time of 2 seconds.
Figure 5:
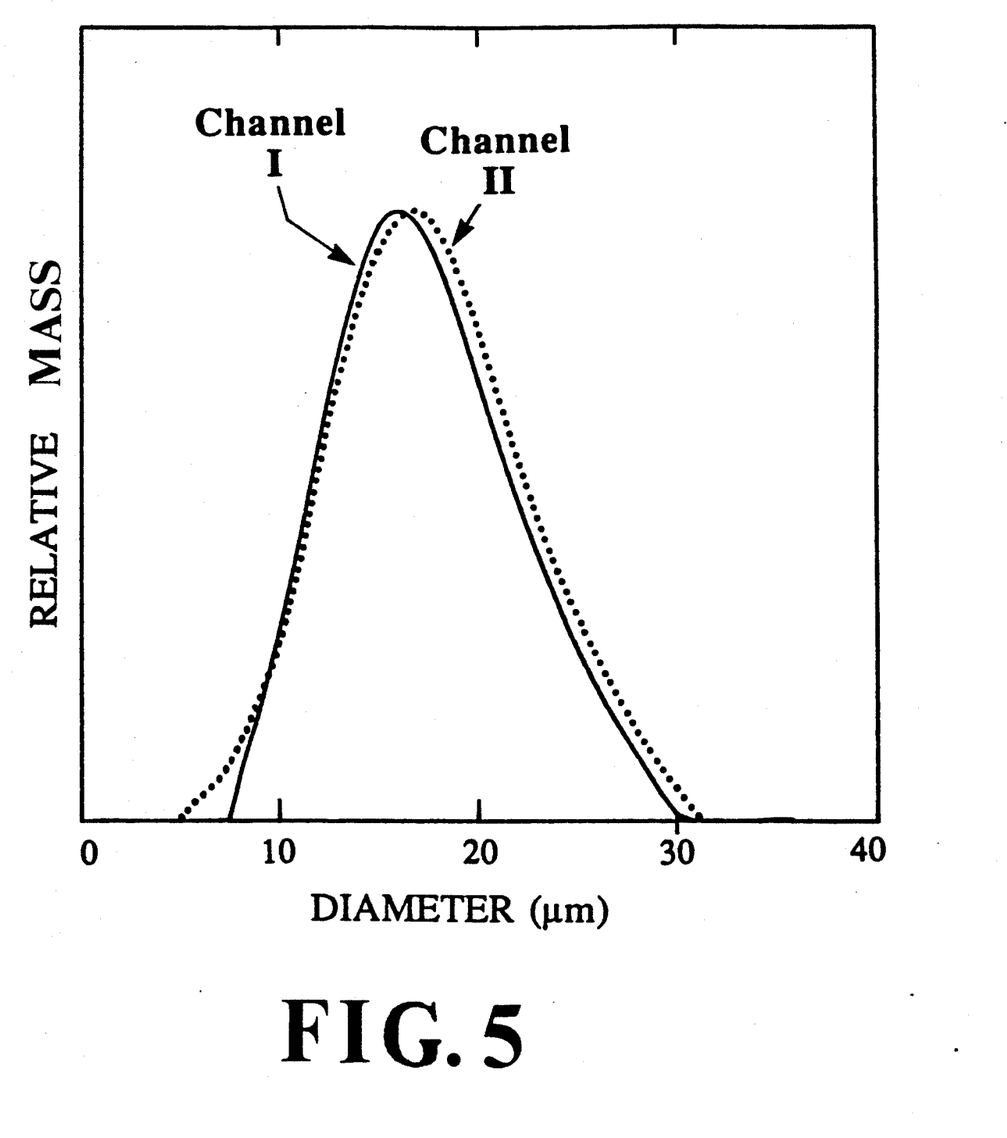
FIG. 5 is a graph comparing the size distribution curves for 5-50 μm glass bead samples using two different channels.

FIGS. 3 and 4 show fractograms of the polydisperse glass bead samples with nominal diameter ranges of 5-30 μm and 5-50 μm, respectively. Both fractograms were obtained with the uniform channel, channel I, at a flowrate of 10.3 mL/min and with a stopflow time of 2 seconds. The 5-30 μm sample, having a density of 2.5 g/mL, was obtained at a rotation rate of 222 rpm. Under these conditions, the $G'\Delta \rho'$ value is exactly the same as the $G\Delta \rho$ applicable to the polystyrene latex standards represented by line "a" in FIG. 2. Since the latter plot fixes a relationship between retention time and particle diameter that applies to the glass bead sample, a particle diameter scale can be readily applied to FIG. 3 as shown along the upper horizontal axis. This scale verifies that most of the glass spheres fall in the range of 5-50 μm as specified by the supplier.

The fractogram (FIG. 4) of the 5-50 μm sample (density 2.45 g/mL) was obtained at 224 rpm. The $G'\Delta \rho'$ value here also corresponds very closely to plot "a" in FIG. 2. The diameter scale obtained from the calibration plot is again shown on the upper horizontal axis. Based on this scale, it appears that most of the spheres have diameters from 20-50 μm with only a minor part of the population having a diameter less than 15 μm.

Fractions were collected from the elution stream in both of the above runs in order to examine the bead diameters microscopically and confirm the validity of the present calibration procedure. Twenty-seven fractions were collected from each sample and a detailed microscopic examination was carried out on these fractions. Results are shown in Table II for about one-third of the fractions. The positions of the reported fractions are shown in the fractograms of FIGS. 3 and 4 and identified by a fraction number. Table II tabulates the microscopically determined diameters (based on a count of from 20 to 30 spheres for each fraction) and compares these to the diameters based on the proposed calibration procedure. The agreement is excellent, thus confirming in large measure the validity of the density compensation approach to calibration.

TABLE II

Comparison of Glass Bead Diameters of Collected Fractions Based on Calibration Procedure and on Microscopy

| fraction | time (min) | diameter based on calibration (μm) | diameter based on micrograph (μm) |
|----------|-----------|-----------|-----------|
| A. Fractions from 5-30 μm Sample, FIG. 3 | | | |
| 2 | 4.10-4.40 | 32.60-29.89 | 32.50 ± 1.65 |
| 4 | 4.70-5.00 | 24.92-25.54 | 24.92 ± 2.97 |
| 7 | 5.60-5.90 | 22.21-20.83 | 21.00 ± 1.25 |
| 11 | 6.80-7.10 | 17.50-16.59 | 17.46 ± 1.08 |
| 15 | 8.00-8.30 | 14.33-13.69 | 13.61 ± 1.23 |
| 19 | 9.20-9.50 | 12.06-11.60 | 11.70 ± 0.71 |
| 23 | 10.50-10.90 | 10.25-9.79 | 9.69 ± 1.07 |
| 27 | 12.10-12.61 | 8.61-8.19 | 8.44 ± 0.83 |
| B. Fractions from 5-50 μm Sample, FIG. 4 | | | |
| 3 | 2.80-2.90 | 52.11-49.91 | 51.90 ± 0.20 |
| 5 | 3.00-3.10 | 47.87-45.98 | 47.07 ± 1.76 |
| 9 | 3.40-3.50 | 41.04-39.60 | 41.46 ± 2.46 |
| 11 | 3.60-3.70 | 38.25-36.98 | 38.42 ± 2.13 |
| 13 | 3.80-3.90 | 35.79-34.67 | 36.87 ± 2.62 |
| 17 | 4.20-4.30 | 31.65-30.74 | 31.33 ± 1.68 |
| 22 | 4.80-5.00 | 26.85-25.54 | 24.92 ± 1.91 |
| 27 | 6.00-6.30 | 20.41-19.60 | 18.63 ± 1.36 |
| 33 | 8.30-8.70 | 13.69-12.72 | 13.50 ± 0.50 |

A critical test of the calibration procedure that complements microscopy entails a comparison of particle size distribution (PSD) curves obtained from different channels, such as channels I and II of the above example, that differ significantly in structure (uniform versus pinched inlet) and operation (stopflow procedure versus stopless flow injection). Both channels, of course, must be separately calibrated with latex beads or other standards in accordance with the invention. Once S and $t_{r1}$ are obtained by calibration and G is adjusted for density compensation, the size distribution can be obtained from the observed fractogram using equation (7).

Figure 6:
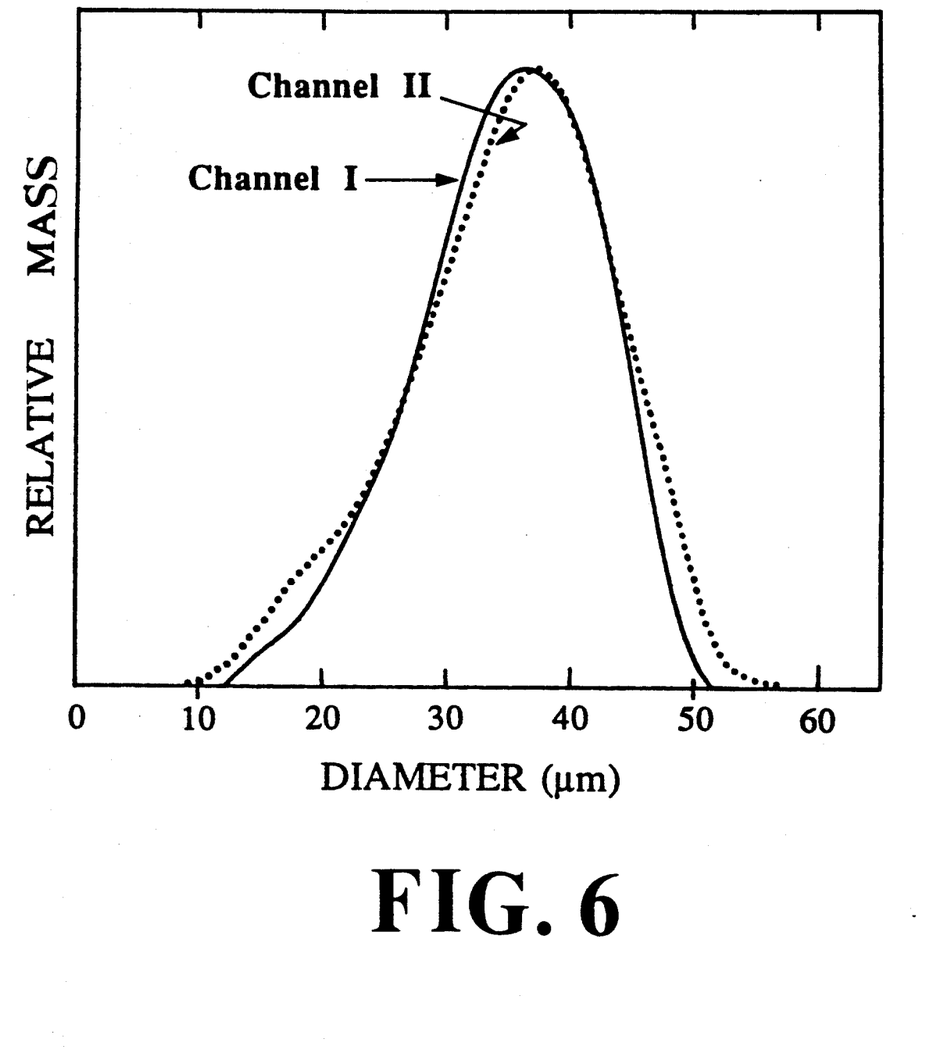
FIG. 6 is a graph comparing the size distribution curves for the 5-50 μm sample obtained from the two channels.

FIG. 6 shows the two PSD curves obtained for the 5–30 μm glass bead sample using channels I and II, respectively. The calibration plots and parameters for these two cases are shown in FIG. 2 and Table I as "a" and "e" for the two respective channels. The input fractogram for the channel I PSD is shown in FIG. 3. The two PSD curves of FIG. 6 are in basic agreement in support of the 5 μm lower and 30 μm upper cutoff diameters for the sample. They differ by about 1 μm on the diameter of the peak of the distribution, which appears to lie in the vicinity of 15 or 16 μm. Overall, the agreement of the two PSD curves is very good.

Although preferred embodiments of the present invention have been illustrated and described, it is to be understood that the present disclosure is made by way of example and that various other embodiments are possible without departing from the subject matter coming within the scope of the following claims, which subject matter is regarded as the invention.

I claim:

1. A procedure for determining the size and size distribution of test particles by using a test sedimentation field-flow fractionation channel through which a liquid carrier stream flows, said procedure comprising carrying out at least one calibration run in which at least one calibration sample of particles of known density and size is injected into a liquid carrier stream flowing through a calibration sedimentation field-flow fractionation channel, wherein the acceleration G acting on the calibration sample during the calibration run and the density difference $\Delta\rho$ between the particles of the calibration sample and the liquid carrier of the calibration run are known so that the product $G\Delta\rho$ for the calibration run has a determined value, and further wherein the calibration channel is the test channel or a duplicate channel having essentially the same dimensions as the test channel or a similar channel having a thickness that is about the same as the thickness of the test channel with the linear velocity of the liquid carrier in the similar channel being maintained essentially the same as the linear velocity of the liquid carrier in the test channel;

measuring retention time or retention volume of particles of different known sizes in the calibration sample;

using the measured retention times or retention volumes to develop a calibration relationship expressing retention time or retention volume as a function of particle size;

in a test run, injecting a test sample of test particles into the liquid carrier stream flowing through said test channel, wherein the density difference $\Delta\rho'$ between the test particles and the liquid carrier stream is known, but the test particles have sizes and a size distribution that are unknown;

adjusting the acceleration G' acting on the test sample during the test run such that the product $G'\Delta\rho'$ for the test run is the same as the product $G\Delta\rho$ for the calibration run;

determining the relative concentration of test particles eluted at different times in the test run; and combining this relative concentration of determination with the calibration relationship to calculate the particle sizes and the particle size distribution of the particles in said test sample.

2. A procedure in accordance with claim 1, wherein a plurality of separate, calibration runs are carried out with a plurality of distinct calibration samples of particles being injected into the carrier stream, with each calibration sample containing a uniform, specified particle size that is different from the particle size of other calibration samples, and the retention time or retention volume is measured for each separate calibration sample.

3. A procedure in accordance with claim 1, wherein the calibration relationship is a plot of log $t_r$ versus log d, wherein d is the diameter of the particles of different known sizes in the calibration sample and $t_r$ is the retention time for respective calibration particles measured in the calibration run.

4. A procedure in accordance with claim 1, wherein the calibration relationship is a plot of log $V_r$ versus log d, wherein d is the diameter of the particles of different known sizes in the calibration sample and $V_r$ is the retention volume for respective particles of different sizes measured in the calibration run.

5. A procedure in accordance with claim 1, wherein the calibration relationship is a mathematical expression relating $t_r$ to d, wherein d is the diameter of the particles of different known sizes in the calibration sample and $t_r$ is the retention time for respective calibration particles measured in the calibration run.

6. A procedure in accordance with claim 1, wherein the calibration relationship is a mathematical expression relating $V_r$ to d, wherein d is the diameter of the particles of different known sizes in the calibration sample and $V_r$ is the retention volume for respective calibration particles measured in the calibration run.

7. A procedure in accordance with claim 1, wherein the relative concentration of the test particles eluted during the test run is used to plot a fractogram having a relative particle concentration axis and a retention time axis or a retention volume axis, with the relative particle concentration being plotted versus the retention time or retention volume, and the calibration relationship is used to develop particle size as a second parameter along an axis parallel to or coincident with the retention time axis or the retention volume axis.

8. A procedure in accordance with claim 1, wherein the test sample is comprised mostly of particles that migrate through the channel according to the steric mechanism of sedimentation field-flow fractionation.

9. A procedure in accordance with claim 1, wherein the test sample is comprised mostly of particles having a diameter range from 1 μm to 100 μm.

10. A procedure in accordance with claim 2, wherein the calibration relationship is obtained by measuring the retention times or retention volumes of a series of latex standards.

11. A procedure in accordance with claim 10, wherein the calibration relationship is obtained by measuring the retention times or retention volumes of a series of polystyrene latex standards.

12. A procedure for determining the size and size distribution of test particles using a test sedimentation field-flow fractionation channel through which a liquid carrier stream flows, said procedure comprising carrying out at least one calibration run in which at least one calibration sample of particles of known density is injected into a liquid carrier stream flowing through a calibration sedimentation field-flow fractionation channel, wherein the acceleration G acting on the calibration sample during the calibration run and the density difference $\Delta\rho$ between the particles of the calibration sample and the liquid carrier of the calibration run are known so that the product $G\Delta\rho$ for the calibration run has a determined value, and further wherein the calibration channel is the test channel or a duplicate channel having essentially the same dimensions as the test channel or a similar channel having a thickness that is about the same as the thickness of the test channel with the linear velocity of the liquid carrier in the similar channel being maintained essentially the same as the linear velocity of the liquid carrier in the test channel;

collecting separate fractions of the carrier stream and calibration sample flowing from said calibration channel;

measuring retention time or retention volume for the separate fractions;

experimentally determining an average diameter of the particles in each of said fractions;

using the measured retention times or retention volumes and the determined diameter of the particles to develop a calibration relationship expressing retention time or retention volume as a function of particle diameter;

in a test run, injecting a test sample of test particles in the liquid carrier stream flowing through said test channel, wherein the density difference $\Delta\rho'$ between the test particles and the liquid carrier stream is known, but the test particles have sizes and a size distribution that are unknown;

adjusting the acceleration $G'$ acting on the test sample during the test run such that the product $G'\Delta\rho'$ for the test run is the same as the product $G\Delta\rho$ for the calibration run;

determining the relative concentration of test particles eluted at different times in the test run; and combining this relative concentration determination with the calibration relationship to calculate the particle sizes and the particle size distribution of the test particles in said test sample.

13. A procedure for producing a calibration relationship for use with sedimentation field-flow fractionation channels having similar dimensions, said procedure comprising carrying out at least one calibration run in which at least one calibration sample of particles of known density and size is injected into a liquid carrier stream flowing through one of the sedimentation field-flow fractionation channels, wherein the acceleration G acting on the calibration sample during the calibration run and the density difference $\Delta\rho$ between the particles of the calibration sample and the liquid carrier of the calibration run are known so that the product $G\Delta\rho$ for the calibration run has a determined value;

measuring retention time or retention volume of particles of different known sizes in the calibration sample; and using the measured retention times or retention volumes to develop a calibration relationship expressing retention time or retention volume and particle size.

14. A procedure in accordance with claim 13, wherein the calibration relationship is a plot of log $t_r$ versus log d, wherein d is the diameter of the particles of different known sizes in the calibration sample and $t_r$ is the retention time for respective particles measured in the calibration run.

15. A procedure in accordance with claim 13, wherein the calibration relationship is a plot of log $t_r/t^0$ versus log d, wherein d is the diameter of the particles of different known sizes in the calibration sample, $t_r$ is the retention time for respective particles measured in the calibration run and $t^0$ is void time.

16. A procedure in accordance with claim 13, wherein the calibration relationship is a plot of log $V_r$ versus log d, wherein d is the diameter of the particles of different known sizes in the calibration sample and $V_r$ is the retention volume for respective particles measured in the calibration run.

17. A procedure in accordance with claim 13, wherein the calibration relationship is a plot of log $V_r/V^0$ versus log d, wherein d is the diameter of the particles of different known sizes in the calibration sample, $V_r$ is the retention volume for respective particles measured in the calibration run and $V^0$ is void volume.

* * * * *